United States Patent [19]

Loftus

[11] 4,365,508
[45] Dec. 28, 1982

[54] LIMPNESS DETECTOR FOR DOCUMENTS AND THE LIKE

[75] Inventor: Peter J. Loftus, Levittown, Pa.

[73] Assignee: Brandt, Inc., Bensalen, Pa.

[21] Appl. No.: 174,595

[22] Filed: Aug. 1, 1980

[51] Int. Cl.³ .............................................. G01N 3/20
[52] U.S. Cl. ..................................... 73/159; 73/849; 73/852
[58] Field of Search ................. 73/812, 849, 852, 159; 194/4 R

[56] References Cited

U.S. PATENT DOCUMENTS

| | | | |
|---|---|---|---|
| 1,857,669 | 5/1932 | Sundback | 73/849 |
| 2,950,794 | 8/1960 | Timms | 194/4 R |
| 3,363,458 | 1/1968 | Scharf et al. | 73/159 |
| 3,528,145 | 9/1970 | Troope et al. | 73/159 |
| 3,944,039 | 3/1976 | Houghtaling | 194/4 R |

Primary Examiner—Anthony V. Ciarlante
Attorney, Agent, or Firm—Weinstein & Sutton

[57] ABSTRACT

A limpness detector for examining documents at high speed. A pair of rollers having star-like cross-sectional configurations comprised of substantially V-shaped projections and interspaced V-shaped grooves are cooperatively arranged so that the projections of one of said rollers at least partially enter into the grooves of the other. The rollers are rotated in a synchronous manner. One swingably mounted roller is preferably yieldably urged toward the other. Documents to be examined are fed between the rollers and, depending upon their relative limpness or stiffness, serve to "lift" the swingable roller such that the amount of displacement between the rollers is a function of document limpness. Sensor means is utilized to detect the amount of displacement. Threshold detection circuitry is provided to facilitate calssification of the documents into limp, moderately stiff and stiff documents, for example. The apparatus may also be utilized to detect the presence of overlapping and/or multiply-fed documents.

34 Claims, 25 Drawing Figures

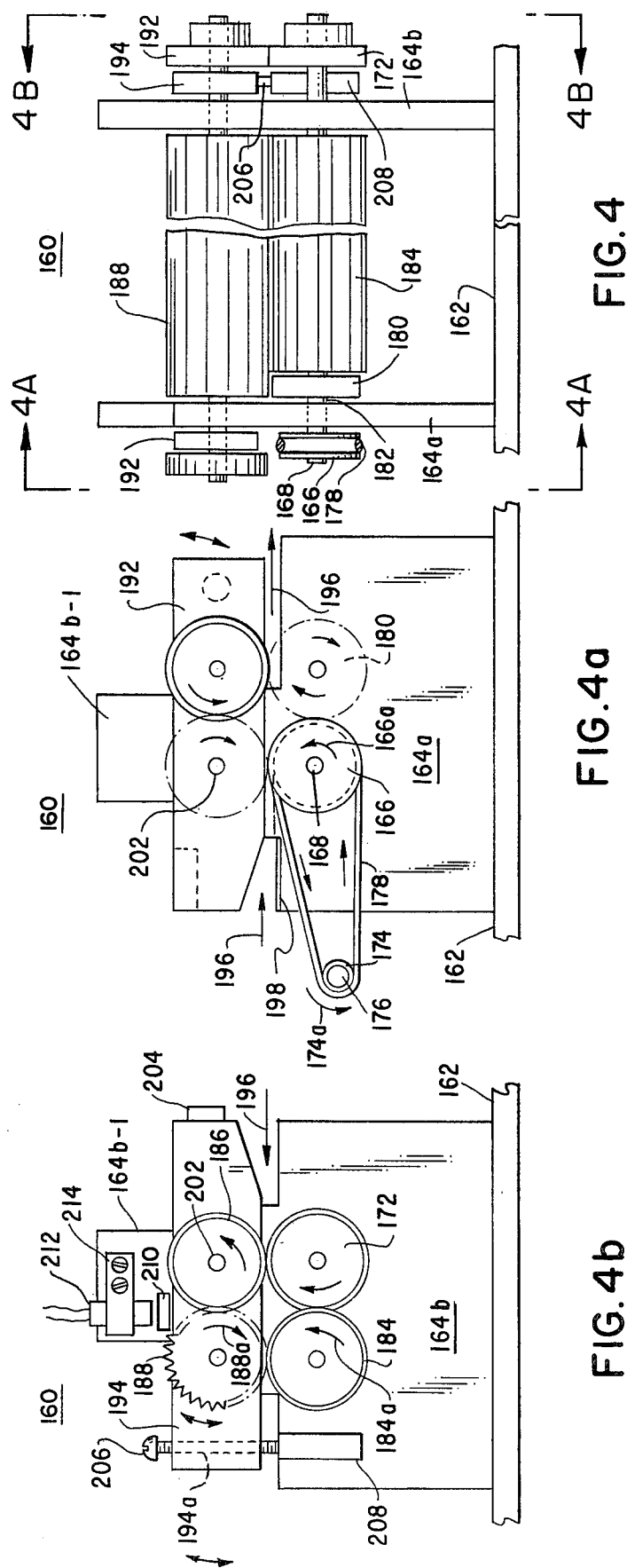

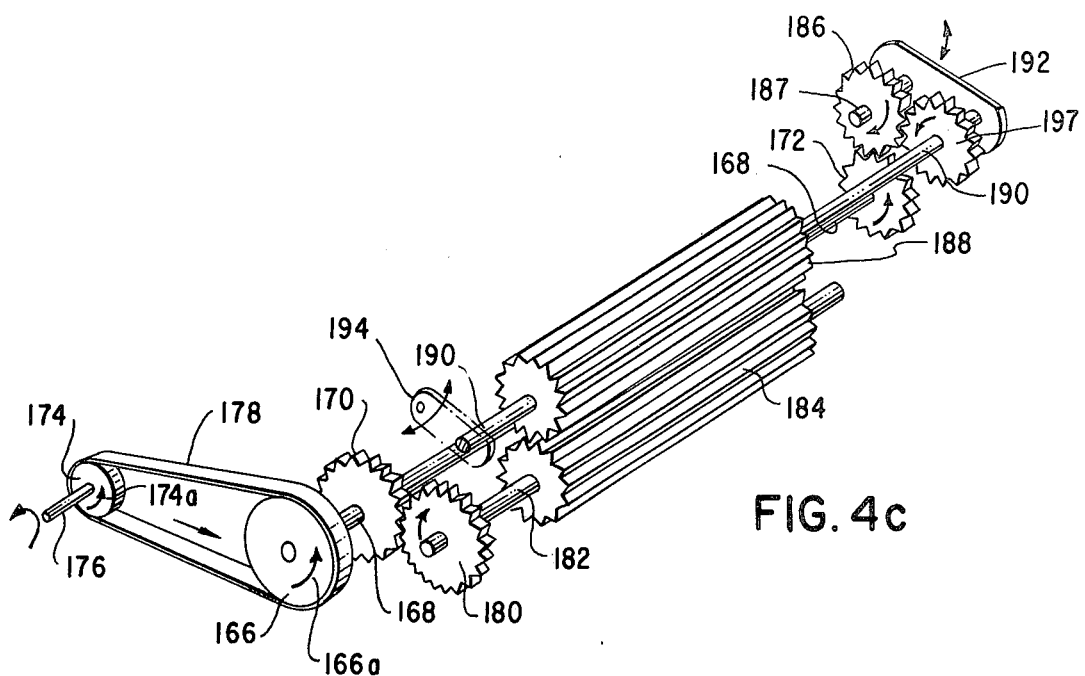
FIG. 4c
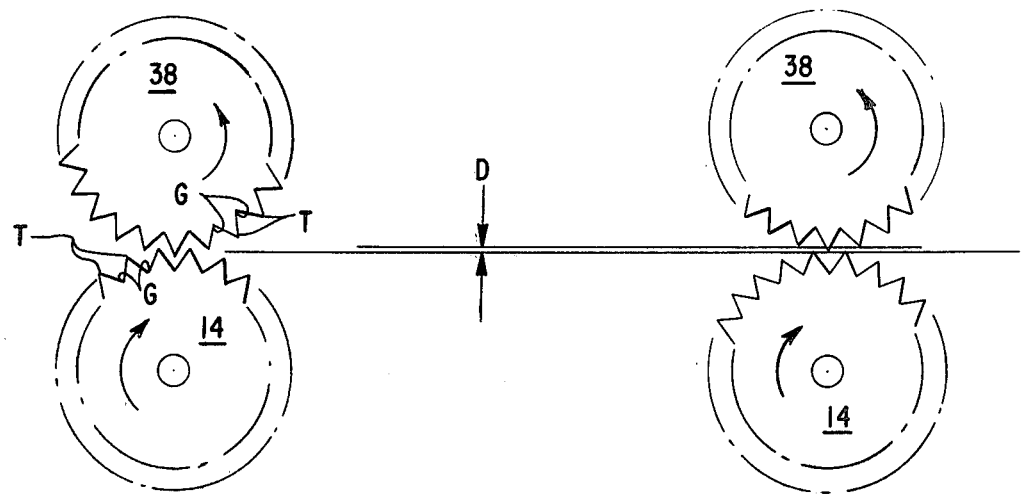
FIG. 5a
FIG. 5b

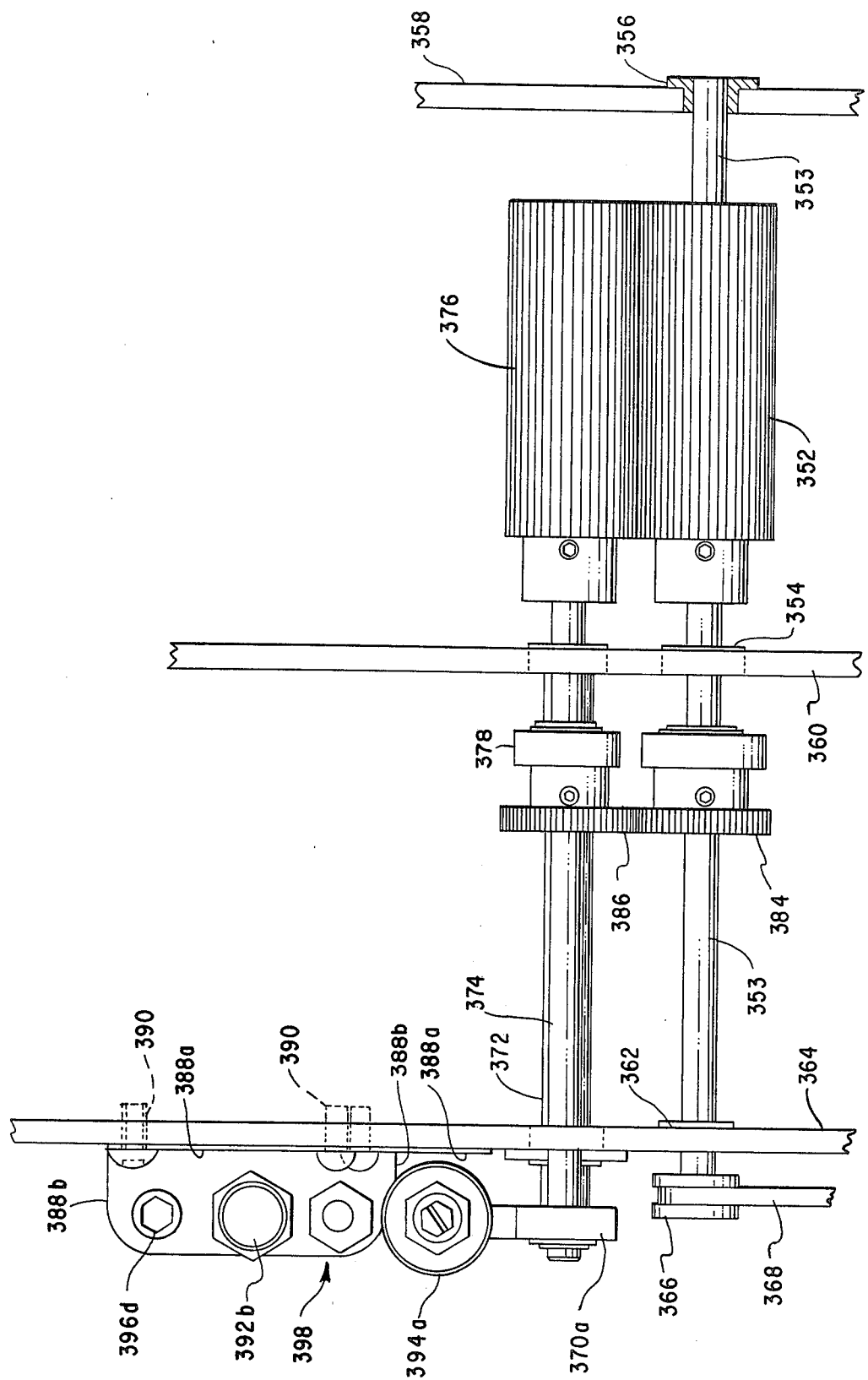

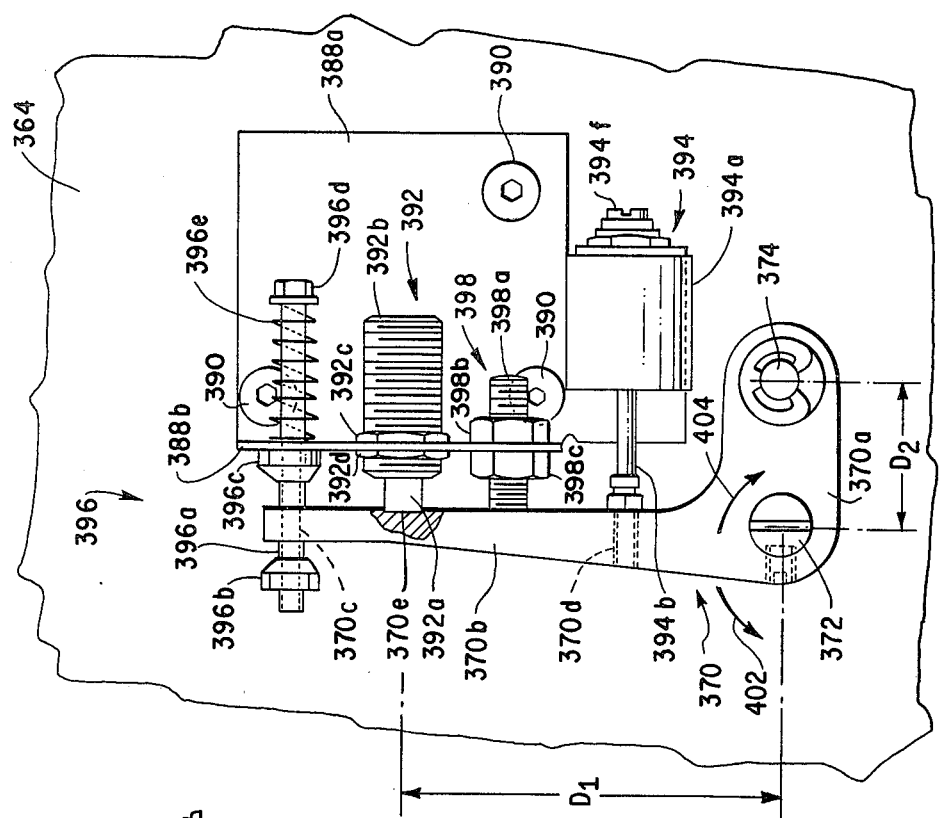
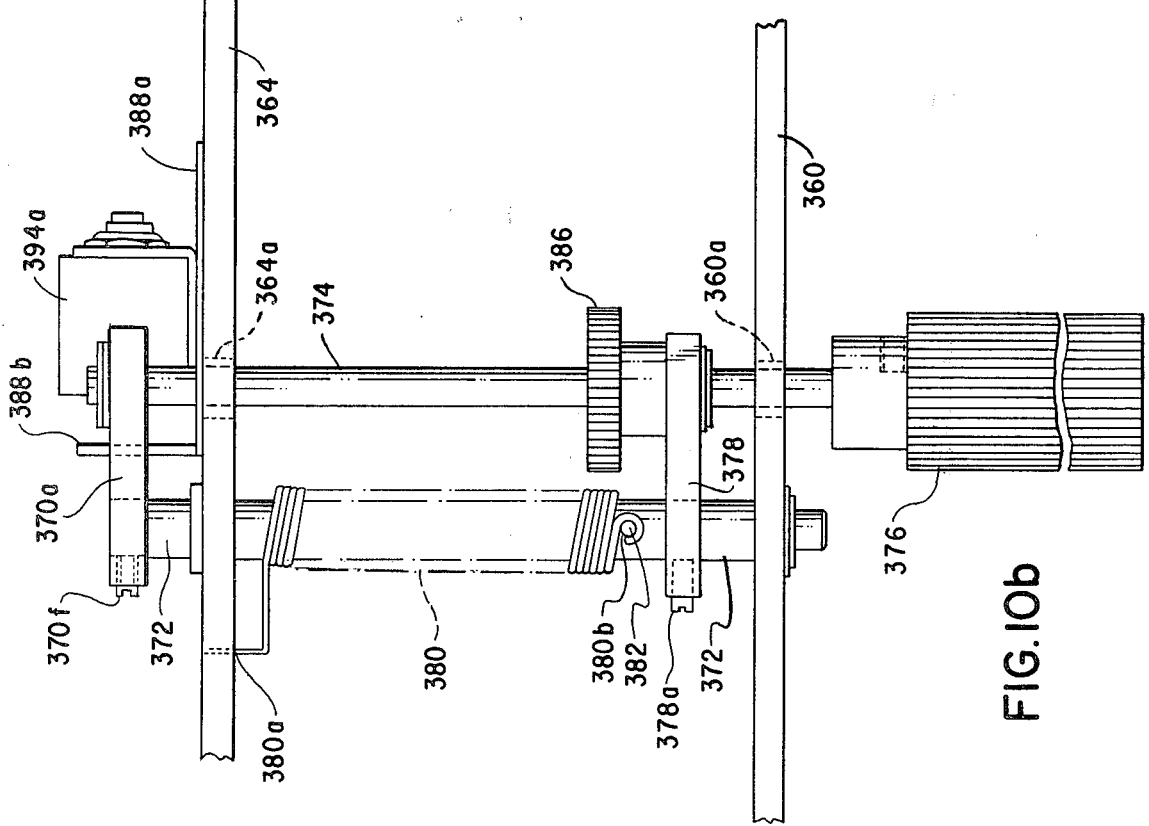
FIG. IOc
FIG. IOb

LIMPNESS DETECTOR FOR DOCUMENTS AND THE LIKE

BACKGROUND OF THE INVENTION

Paper documents which experience a lot of handling are subject to wear as a result of such handling. For example, documents such as paper currency are constantly being handled both manually and by mechanical processing means. Such constant handling subjects the paper currency to wearing and eventually the documents become so worn or limp, that they are no longer serviceable. Worn documents are preferably removed from public use and are destroyed in favor of new paper currency. The advantages of replacement of worn paper currency by new paper currency are both numerous and important, one such advantage being the ease and accuracy of handling new paper currency through mechanical means.

In this connection, it is important to be able to evaluate paper currency at high speed in order to establish its serviceability. Such examinations are typically conducted by institutions such as large banks which are responsible for handling tens of thousands and even hundreds of thousands of pieces of paper currency on a daily basis. Thus, it comes important to be able to process and examine paper currency at high speed and still be able to accurately classify the paper currency into serviceable or unserviceable categories. Only one such limpness detector is known to the present inventor, and comprises a limpness detector in which a pin is utilized to pierce the paper currency such that the force required to pierce through the currency is determinative of the limpness or stiffness of the paper currency. This technique has obvious disadvantages among which are the direct and significant contribution toward the destruction of the paper currency which is directly contrary to the normal objective of preservation of serviceable currency. Also, the technique of piercing the paper currency does not lend itself to high speed handling and to examination of the paper currency while it is moving at such high linear speeds.

BRIEF DESCRIPTION OF THE INVENTION

The present invention is characterized by comprising a limpness detector for paper sheets, documents, paper currency and the like which has the ability of examining sheets at high speed and in a completely non-destructive manner and which is capable of accurately detecting the condition of such documents, thus greatly facilitating the handling of large volumes of such documents in a simple and straight-forward manner. The apparatus embodying the principles of the present invention comprises a pair of rotatably-mounted rollers, each having a star-like cross-sectional configuration comprised, in one preferred embodiment, of alternating substantially V-shaped projections and interspersed substantially V-shaped grooves. The rollers are arranged so that the V-shaped projections of each roller extend at least partially into the V-shaped grooves of the other roller. At least one of the rollers is swingably mounted. A force, which may preferably be gravity, urges the rollers toward one another. Means are provided for synchronously rotating the rollers. Sheets are fed in a single file fashion into the nip formed by the rotating rollers and the sheets act to "lift" the swingable roller away from the remaining roller by an amount which is a function of the relative stiffness or limpness of the sheet being fed therebetween so that the displacement distance between the rollers represents the relative limpness or stiffness of the sheet causing the "lifting." Sensor means is provided for sensing the magnitude of the displacement to develop a signal whose magnitude and/or frequency varies with the size of the physical displacement, said signal being utilized to represent the condition of the sheet being examined. Threshold circuitry may be employed for categorizing the sheets being examined into a desired number of categories, such as fit or unfit; limp, moderately stiff and stiff; as well as other categories, if desired.

The apparatus may also be utilized for purposes of document counting and/or for detecting the presence of double-fed or multiple-fed sheets and/or overlapping sheets. The apparatus may be used as a separate limpness detecting device or may be integrated into document handling and counting apparatus capable of performing other functions substantially simultaneously therewith, such as counting, batching, document authenticity tests, denomination tests and so forth.

OBJECTS OF THE INVENTION AND BRIEF DESCRIPTION OF THE FIGURES

It is, therefore, one primary object of the present invention to provide apparatus for testing documents for limpness and the like while handling such documents at relatively high speeds.

Another object of the present invention is to provide novel star-like roller means which undergo displacement relative to one another as sheets are fed therebetween, said displacement distance accurately representing the relative limpness or stiffness of the sheets.

Still another object of the present invention is to provide novel cooperating roller means for high speed handling and examining of paper sheets fed through the nip formed by said cooperating rollers causing the rollers to be displaced relative to one another by an amount which is a function of the relative stiffness of the documents and wherein electronic means are provided for converting a displacement distance into signals representative of the relative stiffness of said sheets.

Still another object of the present invention is to provide apparatus of the character described hereinabove whereby said apparatus, in addition to detecting the relative limpness of documents, is also adapted to serve as means for: counting; determining the presence of overlapping documents; and determining the presence of multiply-fed documents.

The above, as well as other objects of the present invention, will become apparent when reading the accompanying description and drawings in which:

FIG. 4 shows an end view of another alternative embodiment of the present invention.

FIG. 4a shows a side view of the embodiment of FIG. 4 looking into the direction of arrows 4a—4a.

FIG. 4b shows a side view of the embodiment of FIG. 4 looking into the direction of arrows 4b—4b.

FIG. 4c is a perspective view of a portion of the embodiment of FIG. 4b.

FIGS. 5a and 5b show the positions respectively occupied by the sensor gears when handling no documents and when handling very stiff documents, which figures are useful in describing the operation of the present invention as shown in FIGS. 1a and 1b.

FIGS. 10a, 10b and 10c are front elevational, top plan and left-hand side elevational views respectively of another alternative embodiment of the present invention.

DETAILED DESCRIPTION OF THE INVENTION AND THE PREFERRED EMBODIMENTS THEREOF

Figure 1A:
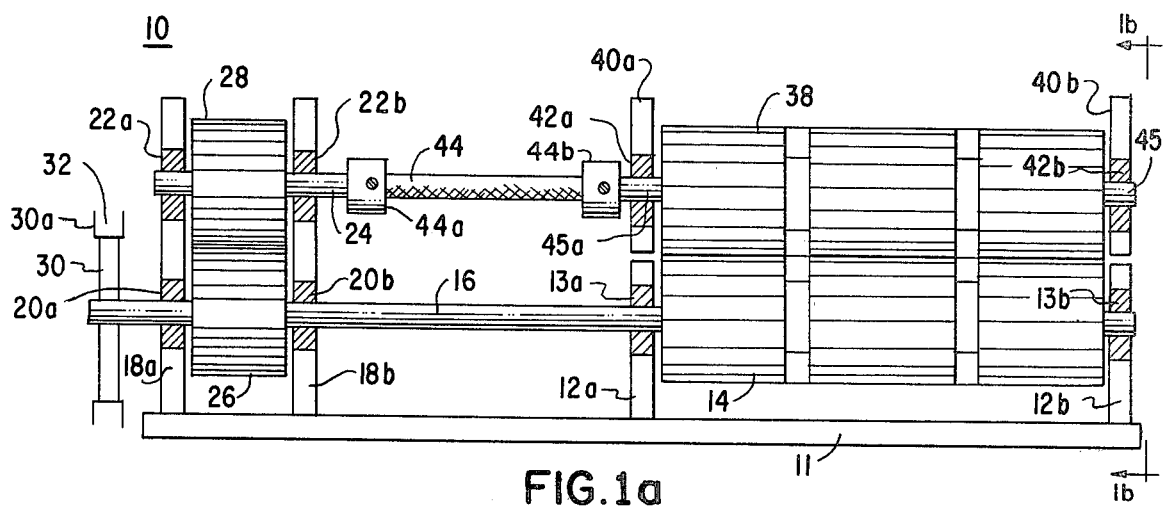
FIG. 1a is a front view of a limpness detection device embodying the principles of the present invention.
Figures 1B, 1C:
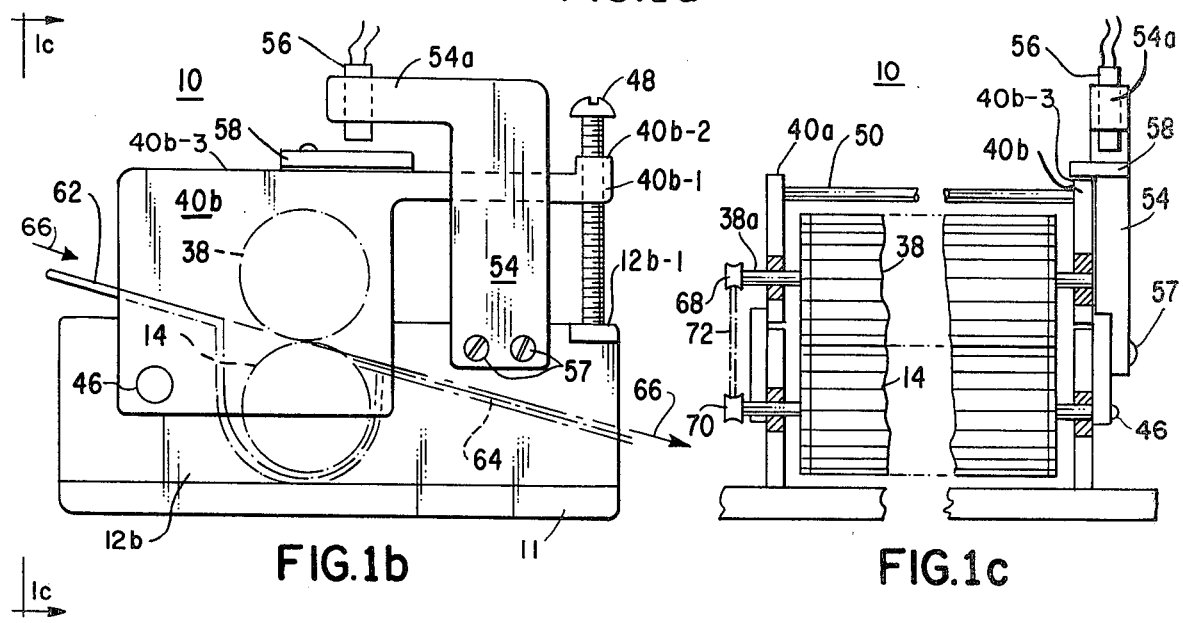
FIG. 1b shows an end view of the limpness detector of FIG. 1a looking in a direction of arrows 1b–1d.
FIG. 1c is an end view of the limpness detector of FIG. 1b looking in a direction of arrows 1c—1c.

FIGS. 1a and 1b show a limpness detector 10 embodying the principles of the present invention and being comprised of a base member 11 having a first pair of supports 12a and 12b mounted upon base 11 and each being provided with a pair of bearings 13a and 13b for freewheelingly supporting the shaft 16 of a first sensor gear 14. Gear 14 is an elongated substantially cylindrical member having a cross-sectional configuration which is shown best in FIG. 5a as being comprised of teeth T in the form of substantially V-shaped projections, said teeth T being spaced apart by interspersed substantially V-shaped grooves G. Sensor gear shaft 16 is an elongated shaft freewheelingly mounted at its left end by bearings 20a and 20b provided within a pair of uprights 18a and 18b secured upon base member 11. The upper ends of supports 18a and 18b are further provided with a second pair of bearings 22a and 22b for freewheelingly mounting a shaft 24. Shaft 16 has secured thereto a gear 26 arranged to rotate with the rotation of shaft 16. Shaft 24 has secured thereto a driven gear 28 adapted to rotate shaft 24 when driven by gear 26. Gears 26 and 28 are driven between support plates 18a and 18b as shown.

Figure 6:
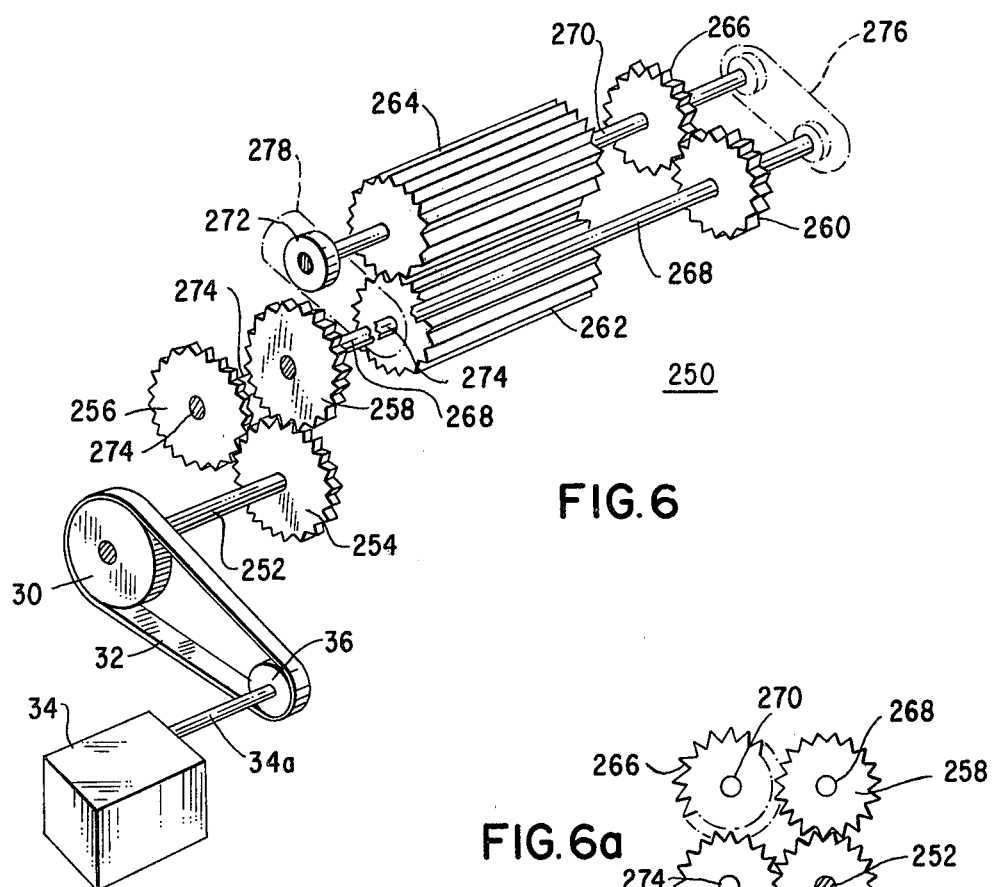
FIG. 6 shows a perspective view of still another embodiment of the present invention.

Shaft 16 extends to the left of mounting plate 18 and has secured thereto a pulley 30. A belt 32 arranged about the outer periphery 30a of pulley 30 is designed to be entrained about a pulley (not shown) mounted upon the output shaft of a drive motor (not shown) so as to rotate the pulley (not shown) upon the output shaft of the drive motor and the driven pulley 30. This arrangement is shown in FIG. 6 wherein the drive motor is shown at 34, the drive motor output shaft is shown at 34a, the drive motor output pulley is shown at 36, the belt is shown at 32 and the driven pulley is shown at 30.

A second sensor gear 38 is mounted between a pair of swingable mounting plates 40a and 40b, each being respectively provided with a bearing 42a and 42b for freewheelingly mounting sensor gear 38 thereto. A flexible drive shaft 44 has its lefthand collar 44a coupled to shaft 24 driven by gear 28 and has its righthand collar 44b coupled to the lefthand end 45a of sensor gear shaft 45.

The mounting plate 40b is shown in FIG. 1b and is provided with a pivot pin 46 which is pivotally secured to side plate 12b thereby swingably mounting plate 40b to plate 12b. Plate 40a is swingably mounted to plate 12a in a similar fashion. The righthand end of plate 40b relative to FIG. 1b, is provided with an elongated projection 40b-1 having a tapped opening 40b-2 for receiving threaded fastening member 48 whose lower end is adapted to engage surface 12b-1 of side plate 12b. As shown in FIG. 1c, the plates 40a and 40b, in addition to being swingably mounted by pivot pin 46, are secured to one another by cross-piece 50. Thus, when the fastening member (screw) 48 is adjusted to lift or lower arm 40b-1 relative to edge 12b-1 of side plate 12b, this swingable movement is directly imparted to sideplate 40a in order to adjust the position of sensor gear 38 relative to sensor gear 14 and further to be assured that the axis of sensor gear 38 is maintained in parallel with the axis of sensor gear 14.

A supporting arm 54 is secured to sideplate 12b by fastening members 57 and extends substantially vertically upward as shown best in FIGS. 1b and 1c. The upper end of supporting bracket 54 extends to the left, forming supporting arm 54a for positioning and securing proximity detector 56 within an opening provided therefor. The proximity detector 56 has its lower end positioned immediately above a steel plate 58 secured to the top edge 40b-2 of swingably mounted sideplate 40b. A pair of guide plates 62 and 64 are arranged to guide paper sheets fed from the lefthand side of limpness detector 10 (relative to FIG. 1b), so as to move in a direction shown by arrows 66 through the nip formed by sensor gears 14 and 38, in order to test for document limpness as will be described hereinbelow.

As was mentioned hereinabove in connection with sensor gear 14, it should be understood that sensor gear 38 is provided with teeth T similar to teeth T of gear 14, said teeth being in the form of V-shaped projections, which teeth are separated by interspersed V-shaped grooves G, as can best be seen in FIG. 5a.

The threaded member 48 is adjusted to arrange the gearlike teeth T of the lower and upper sensor gears 14 and 38 in the manner shown best in FIG. 5a so that the gear teeth do not engage one another. However, the spacing between the sensor gears 14 and 38 is adjusted so that the gear teeth T of each sensor gear, at least partially enter into the grooves G of the other sensor gear.

The paper documents which may, for example, be paper currency, move along the guide path represented by arrows 66 by virtue of the guide plates 62 and 64 so as to enter into the nip between the sensor gears 14 and 38. It should be noted that the upper sensor gear 38 and swingably mounted support plates 40a and 40b rest upon surface 12b-1 of the lower support plate 12b by virtue of the threadable fastening member 48 due to the force of gravity exerted upon the swingably mounted plates 40a and 40b and the upper sensor gear 38. As can clearly be seen from a consideration of FIG. 5a, a sheet of paper currency, for example, entering between the sensor gears 14 and 38 is not able to pass freely therebetween without being urged into a corrugated shape by an amount determined by the setting of threaded fastening member 48. As a result, there is a counter force exerted by the paper sheet upon the sensor gears 14 and 38 which force tends to counteract the force exerted upon the paper sheet which tends to urge the paper sheet to assume a corrugated shape. The amount of corrugation experienced by the paper sheet is a function of its relative stiffness or limpness. For example, an extremely limp sheet having a limpness of the order of a sheet of a very light, thin gauge onionskin paper, or a sheet having a limpness of a sheet of facial tissue, is very easily urged into a corrugated shape. The counteracting force exerted by such an extremely limp sheet against the sensor gears 38 and 14 is substantially nil so that the spacing between sensor gears 14 and 38 remained unchanged and the spacing distance between gears 14 and 38 is as shown in FIG. 5a.

On the other hand, if an extremely rigid or stiff sheet is passed between gears 14 and 38, such as for example an extremely stiff sheet of paper or a sheet of stiff cardboard, such as for example a punched card, the force exerted by the sensor gears 38 and 14 upon such a stiff member is significantly less than the force exerted by such a stiff sheet upon the sensor gears 14, 38 14 and 38, whereupon the gears will be caused to move apart to the position shown in FIG. 5b, resulting in a lifting of the sideplates 40a and 40b. The letter D represents the distance moved by roller 38. Plates 40a and 40b are free to be lifted without affecting the driving relationship, due to the employment of flexible drive shaft 44 which continues to impart constant positive drive to upper sensor gear 38 even though upper sensor gear 38 is lifted from the position shown in FIG. 5a to the position shown in FIG. 5b. If desired, the force tending to urge upper sensor gear 38 and lower sensor gear 14 toward one another may be increased beyond the gravitational force by mounting pulleys 68 and 70 respectively upon the lefthand ends of the shafts 45 and 16 upon which the sensor gears 38 and 14 are rotatably mounted. A resilient element such as a rubber band or O-ring 72 is entrained about pulleys 68 and 70 to exert a force upon the sensor gears 38 and 14 tending to urge the sensor gears 38 and 14 toward one another.

Figure 1D:
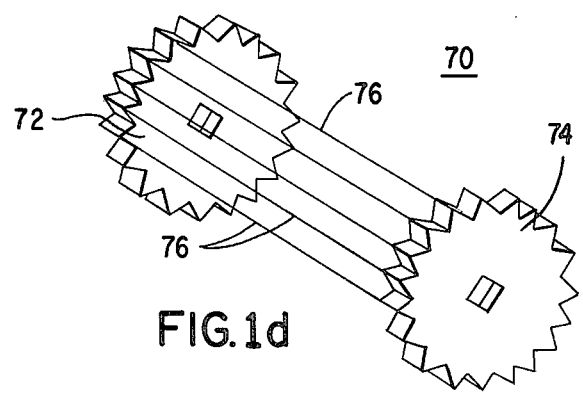
FIG. 1d is a perspective view of an alternative assembly which may be employed, in the limpness detector of FIGS. 1a–1c.

As an alternative embodiment, noting FIG. 1d, the gear members 14 and 38 may each be replaced by a gear-like assembly 70 comprised of a pair of discs 72 and 74 with peripheries similar to those shown in FIG. 5a. Substantially taut wires 76 extend from the free edge of each tooth T of disc 72 to the free edge of an associated tooth T of disc 74. The sensor gears of the design of FIG. 1d are then arranged so that each wire 76 from one of the sensor gears is interspersed between a pair of wires of the cooperating sensor gear in much the same way as the gear teeth T of FIG. 5a of each sensor gear extend at least partially into the groove between adjacent gear teeth. The operation of the alternative embodiment in which the sensor gears 14 and 38 of FIGS. 1a through 1c are replaced by sensor gears of the type shown in FIG. 1d, is substantially identical to that shown in FIGS. 1a–1c, wherein the wires 76 tend to urge a sheet fed therebetween into a corrugated configuration and wherein the sheet fed therebetween exerts a counterforce, which is a function of the relative stiffness of the sheet 70 from a nominal gap or separation position shown in FIG. 5a to some position between that shown in FIG. 5a and the maximum separation gap shown in FIG. 5b.

In order to convert the separation distance into a more readily usable form, the limpness detector 10 employs a steel sheet 58 in cooperation with proximity detector 56. One suitable detector circuit 80 which may be employed therein is shown in simplified fashion in FIG. 2 and is comprised of a transformer-type structure 81 having a primary winding 82 and a secondary winding 84. The magnetic coupling between windings 82 and 84 is controlled by the position occupied by ferromagnetic (steel) sheet 58 relative to windings 83 and 84. A signal source 86, which may for example be a high frequency oscillator, is coupled to primary winding 82. Secondary winding 84 is coupled to a fullwave diode bridge 88 for converting the signal developed in secondary winding 84 into a full wave rectified signal. Resistor element R1 and capacitor element C1 smooth the full wave rectified signal. The signal taken from the common terminal 87 between R2 and C1 is applied to an output display means 90 which may, for example, be a threshold detection circuit capable of generating an output signal when the input signal provided thereto is above a predetermined threshold.

Figure 2:
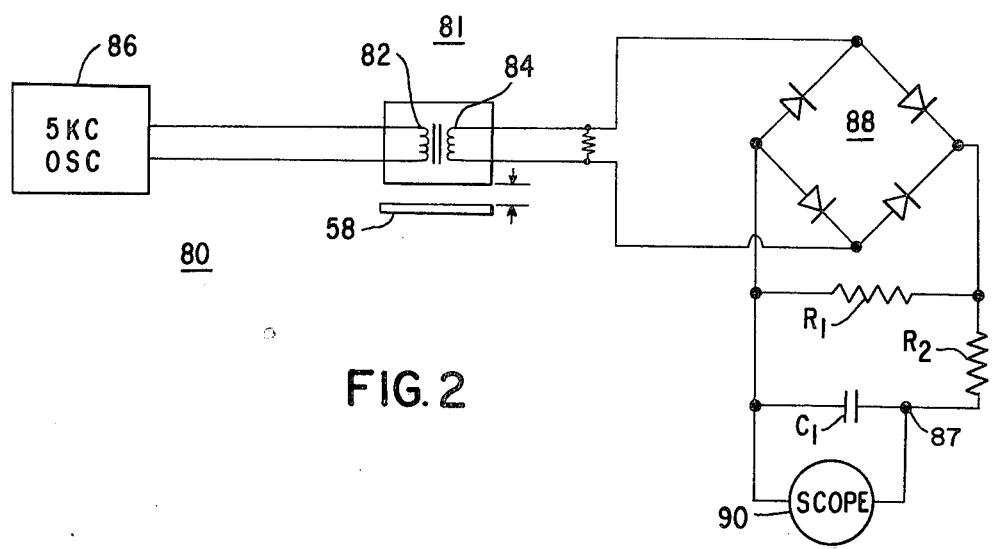
FIG. 2 shows a schematic view of an electronic detector which may be employed with the limpness detector of FIGS. 1a and 1b.
Figure 2A:
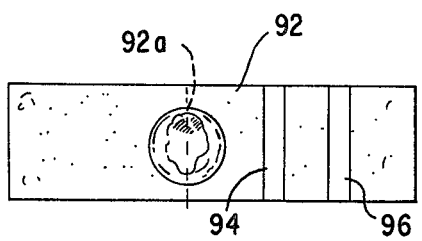
FIG. 2a is a plan view of a sheet of paper currency and FIGS. 2b through 2d are waveform diagrams useful in explaining the operation of the apparatus of FIGS. 1a and 2.
Figure 2B:
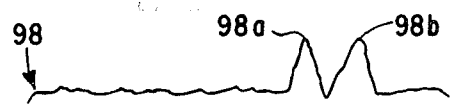

The sensitivity of the circuit 80 can be appreciated from FIG. 2a in which a sheet of paper currency 92 was modified by placing two thin strips 94 and 96 at spaced distances therealong. FIG. 2b shows the waveform developed by display 90 such as a cathode ray oscilloscope coupled across capacitor C1 of circuit 80 of FIG. 2. The two distinct peaks 98a and 98b of waveform 98 represent the increased stiffness of paper currency 92 at the positions occupied by the strips 94 and 96 secured to paper currency 92.

Figure 2C:
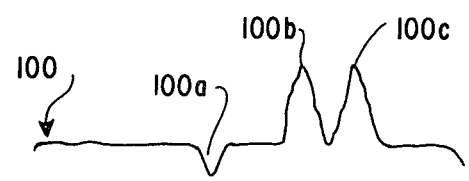

Sheet 92 which was originally relatively stiff, was then deliberately folded in the center many times in order to make the center portion of the sheet at fold 92a very limp. The sheet 92 was then fed to the limpness detector apparatus 10 of FIG. 1, said fold being shown in the sheet 92 as occupying the position 92a. The sheet was then run through the apparatus 10 of FIG. 1 and was found to develop the waveform 100 shown in FIG. 2c. It can be seen that a dip in the waveform at 100a resulted from the significantly reduced stiffness of the paper currency in the region of fold 92a. The peaks 100b and 100c correspond to the positions occupied by the added strips 94 and 96.

Figure 2D:
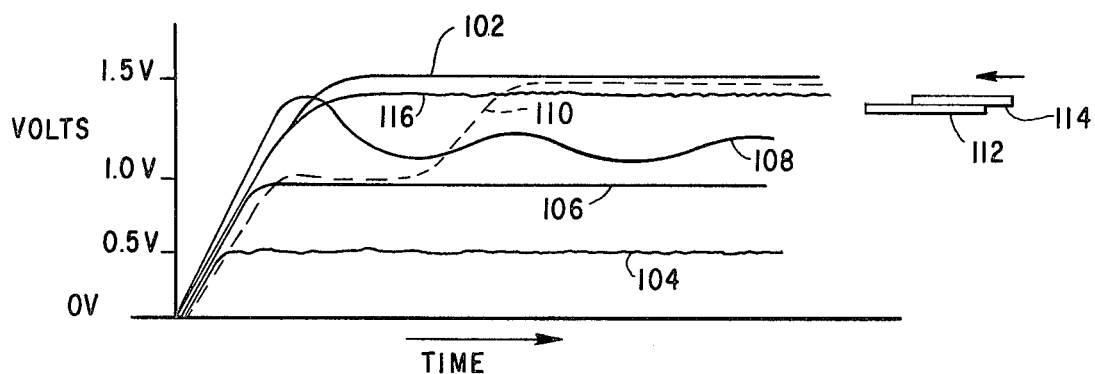

FIG. 2d shows a group of waveforms detected by the circuit 80 of FIG. 2 through the employment of an oscilloscope coupled across the capacitor C1. Waveform 102 represents the upper sensor gear 38 being held in the position shown in FIG. 5b by lifting arm 40b-1 of FIG. 1b by the operator's hand. Waveform 104 represents the signal on the oscilloscope developed by one sheet of onionskin paper. Two sheets of onionskin paper fed simultaneously developed the waveform 106. A single sheet of paper currency in fairly good condition developed the signal 108. Waveform 110 resulted from the feeding of two sheets of paper currency 112 and 114 overlapping one another in the manner shown. Waveform 116 resulted from the feeding of a relatively stiff postcard through the sensing device. Based upon the results obtained, it was found that paper currency under test may be categorized as being stiff if the signal developed by the sensing device is greater than 1.25 volts for a period of greater than 10 to 20 milliseconds.

Paper currency may be categorized as limp if the output signal developed is 0.50 volts or less. Alternatively, paper currency may be considered as being limp if the signal exceeds 0.50 volts but drops below 0.5 volts. As a result the multi-threshold categorizing circuit 120 of FIG. 3 was developed, said circuit being comprised of comparators 130, 132 and 134, each being adapted to compare the incoming signal against an associated threshold level. The circuit 80 of FIG. 2 has been substantially reproduced in FIG. 3 for purposes of simplicity. As noted in both FIGS. 2 and 3 the output signal is derived from the common terminal A between resistor R2 and capacitor C1. This common terminal A is coupled in common to the non-inverting inputs 130a, 132a and 134a of comparators 130, 132 and 134. A threshold level is applied to the inverting input 130b of comparator 130. The threshold level is determined by resistors R4 and R5 coupled between the +5 volt D.C. and ground terminals. An adjustable slider arm 124 is coupled between resistor R5 and inverting input 130b. In a similar fashion, slider arm 126 couples inverting input 132a to resistor R6 which is coupled in series with resistor R3 between +5 volts D.C. and ground potential. Similarly, resistors R2, R7 and R8 are coupled between +5 volts D.C. and ground potential and slider arm 128 couples inverting input 134b of comparator 134 to resistance R7. Each of the reference levels applied to the inverting inputs 130b, 132b and 134b are established substantially as were described hereinabove for one particular embodiment wherein the threshold level at 134b is 0.5 volts, the threshold level at 132b is just under 1 volt and the threshold level at 130b is 1.5 volts.

In the event that the detected level is above 1.5 volts, the output 130e of comparator 130 goes to ground. This level is inverted to a high level by invertor 136 which is applied to one input of a NOR gate 140. NOR gate 140 and a second NOR gate 142 collectively form a bistable circuit. When a high level is applied to input 140a of NOR gate 140, it is inverted to a low level. A low level is applied to input 142b of NOR gate 142 through normally closed switch 148 coupled between input 142b, and resistor R14 at one of its contacts and coupled to ground at its other contact. This level is inverted to a high level causing the output 142c of NOR gate 142 to go high. This high level is applied to the remaining input 140b of NOR gate 140. Thus, the output of NOR gate 140 goes high. This high level is applied to input 142a of NOR gate 142. This level is inverted to a low level causing a low level to be applied at input 140b. Since its output is already high, this condition is maintained. The high level at output 140c of NOR gate 140 is coupled to the base electrode of transistor Q1 through resistor R15 causing transistor Q1 to conduct and thereby establishing a current path between the +5 volt D.C. source, lamp 152, resistor R17 and the collector to emitter path of transistor Q1 to ground. Lamp 152 thus indicates the presence of a document which is too stiff, possibly due to multiply-fed documents. In the event that the output signal appearing at terminal A drops below 1.5 volts, the output 130c of comparator 130 stays low. This condition is inverted by inverter 136 to apply a high level to input 130a of NOR gate 140. This condition is inverted to develop a low output 140c. The low level applied to input 142b of NOR gate 142 is inverted to a high, developing a high level at output 142c which is inverted to a low level at input 140b. The two low levels applied to NOR gate 140 cause its output to be low and thereby maintain transistor Q1 in cutoff.

Comparators 132 and 134 function in a similar fashion wherein their outputs are low when the signal applied to their respective non-inverting inputs 132b, 134b is less than the threshold level applied to the associated inverting inputs 132a, 134a and wherein the output goes high when the signal applied to the non-inverting input 132b, 134b is equal to, or greater than the reference level applied to the associated inverting input 132a, 134a. When the signal applied to the non-inverting input 132b of comparator 132 is high, output 132c goes low causing the output of NAND gate 138 to go high. This high input is inverted to a low input by NOR gate 144 which prevents transistor Q2 from conducting. Similarly, comparator 134 has its output go low when the voltage applied to its non-inverting input 134b is greater than the threshold reference level applied to inverting input 134a whereupon the output of NAND gate 138 is high which level is inverted to a low level input by NOR gate 144, also maintaining transistor Q2 in the cutoff condition. When the threshold levels at either the inverting input 132a or the inputs of comparators 132 and 134 are both higher than the input level applied to terminal A, both inputs to NAND gate 138 are high, causing its output to go low. The low output is inverted at 144a by NOR gate 144 to cause the output of NOR gate 144 to go high and thereby cause transistor Q2 to conduct, whereupon lamp 154 is illuminated to indicate the passage of a limp document. When output 132c is high, diode D1 places a high level at both inputs of gate 138, operating the lamp 154 in the manner described above.

Figure 3:
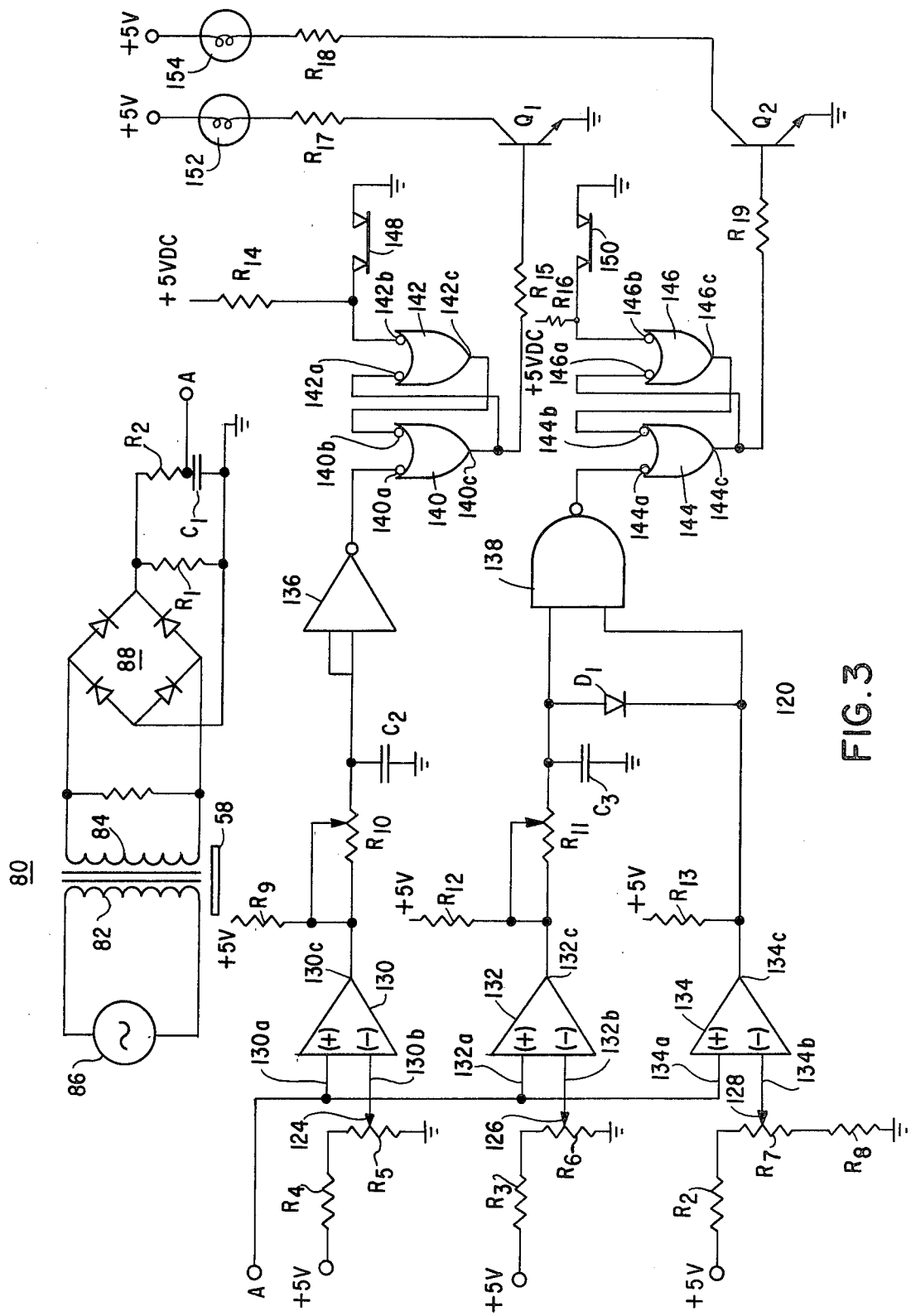
FIG. 3 shows a schematic diagram of a detector circuit for detecting documents for limpness and for categorizing the documents into satisfactory, too limp, and too stiff categories.

Thus, it can be seen that the circuitry 120 of FIG. 3 provides a lamp illumination for documents which are too limp, and for documents which are too stiff, while the absence of any lamp illumination indicates the passage of a satisfactory document. If desired, a third lamp and associated logic circuit (not shown) can be provided to indicate the passage of documents of acceptable stiffness. For example, the output of Q2 may be inverted by an additional transistor (not shown) and having a lamp (not shown) coupled between the additional transistor and a suitable power source.

The alternative embodiment 160 of FIGS. 4 through 4c shows an arrangement in which the flexible shaft 44 of FIG. 1a may be eliminated. As shown therein, the detector 160 is provided with a base-plate 162 supporting a pair of upright plates 164a and 164b. A pulley 166 has its shaft 168 mounted for rotation within a suitable bearing (not shown) provided in upright 164a, shaft 168 extending through to the opposite side plate 164b and being journaled in a suitable bearing (not shown) provided in upright 164b. The opposite end of shaft 168 supports and rotates gear 172. Gear 170 is positioned in close proximity to pulley 166 and rotates with the rotation of shaft 168 (FIG. 4c).

Pulley 166 is driven by pulley 174 mounted to the output shaft 176 of a motor (not shown). Drive belt 178 is entrained about pulleys 174 and 166. Pulleys 174 and 166 rotate counter-clockwise as shown by the arrows 174a and 166a. As a result, sensor gear 184 rotates clockwise (see arrow 184a, FIG. 4b) and sensor gear 188 rotates counterclockwise (see arrow 188a, FIG. 4b) in order to provide proper drive for documents moving along the document feed path indicated by arrows 196 and guided by document guide plate 198 in order to move documents between the nip formed between sensor gears 188 and 184. The sensor gear 188 is adapted to be swingably mounted about an axis 202, said frame carriers 192 and 194 being pivotally mounted about said axis to swingably mount sensor gear 188. The frame carriers 192, 194, are secured to one another, for example, by means of a cross piece 204 shown best in FIG. 4b so as to swing in unison about the pivotal axis 202 and maintain gear 188 parallel to gear 184. Threaded fastener 206 cooperates with a tapped opening 194a in frame carrier 194 in order to adjust the sensor gears 188 and 184 to establish the displacement gap therebetween. The bottom tip of threaded member 206 rests upon the top surface of a projection 208 extending outwardly from upright 164b. The frame carrier 194 has a steel block 210 secured thereto so as to cooperate with a proximity detector 212 mounted by bracket 214 to the upper end 164b-1 of upright 164b. In the same manner as was previously described, stiff documents cause the sensor gear 188 to be lifted upward relative to the lower sensor gear 184 causing the steel block 210 to move closer to proximity detector 212. Conversely, very limp documents or no documents at all cause the teeth of sensor gear 188 to extend more deeply into the grooves of sensor gear 184 whereupon the steel block 210 is positioned furthest from the proximity detector 212. These signals are utilized to provide relative stiffness or limpness indications of the documents being handled. As can be seen from a consideration of FIGS. 4a, 4b and 4c, positive drive is provided to both sensor gears 188 and 184 without the use of a flexible coupling shaft such as, for example, the flexible shaft 44 shown in FIG. 1a.

With the embodiment of FIGS. 4 through 4c, it was found that relative rotation of the drive gears caused by the swinging movement of sensing gear 188 relative to sensor gear 184 causes the teeth of the drive gears 170, 172, to experience some interference with one another. In order to cure such interference, the design 250 of FIG. 6 was developed in which none of the drive gears are directly connected between the sensor gear shafts and hence the tooth interference which is found to occur in the embodiment of FIGS. 4 through 4c is eliminated as is described hereinbelow.

Figure 6A:
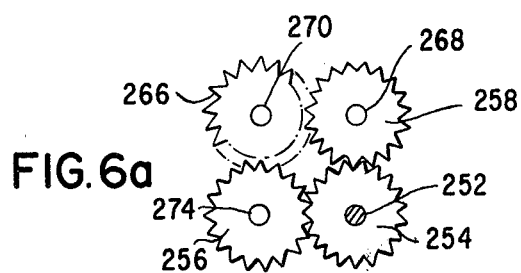
FIG. 6a is an end view showing the positions of the gears of the embodiment of FIG. 6.

Considering the embodiment 250 of FIGS. 6 and 6a, there is provided therein a motor 34 having output shaft 34a for driving pulley 36. A drive belt 32 is entrained about pulley 36 and a second pulley 30 mounted to rotate upon shaft 252. The opposite free end of shaft 252 carries gear 254 which is adapted to mesh with gear 256 mounted to rotate upon shaft 274 and gear 258 mounted to rotate upon shaft 268. Shaft 274 has mounted thereto the lower sensor gear 262.

Shaft 268, which is rotated by gear 258, extends across the apparatus 250 and is provided with gear 260 mounted at its opposite free end. Gear 260 meshes with gear 266 mounted to rotate upon shaft 270. Shaft 270 carries the upper sensor gear 264. The opposite free end of shaft 270 is mounted within a bearing 272 in an upper swingable frame member 278 which is swingable about an axis determined by shaft 268. A second swingable frame member 276 swingably mounts upper sensor gear 264. An end view of the gear arrangement of FIG. 6 is shown in FIG. 6a wherein gear 254 is shown as meshing with gear 256. Gear 254 also meshes with gear 258. Gear 258 is mounted upon shaft 268, the opposite end of which carries gear 260. Gear 260 meshes with gear 266 mounted upon shaft 270. Shaft 274 carries lower sensor gear 262 while shaft 270 carries upper sensor gear 264.

The sensor gears 262, 264 may be solid members of either a solid or hollow core, or alternatively may be comprised of elongated wires as per the embodiment of FIG. 1d. It should further be noted that the sensor gears may also be formed of a variety of materials. For example, the sensor gears may be formed of molded plastic of different diametrical pitch and numbers of teeth. It was found that the runout of the gear outer diameters introduced relatively large signal changes that greatly interfered with the actual signal. Experiments have been conducted with sensor gears having a different number of gear teeth. A first version employed 12 teeth per gear having a diameter of 1.060 inches. A second version contained 18 teeth and had a diameter of 1.020 inches. It should be noted that the fewer the number of teeth the greater the effective beam length of the paper sheets being examined, thereby reducing its apparent stiffness. The 12 tooth gear appeared to result in too soft an arrangement. It presently appears that the 18 tooth 1.020 diameter gear provides optimum results.

The frequency response of the limpness detector 250 is relatively low and the measurement of limpness is preferably averaged over a large portion of the bill. It has been found, however, that the limpness detector picks up limpness due to the center crease found in most notes if its frequency response of the sensor circuit 80 is high enough. As a result, it appears that sensor gears having pointed teeth with an increased number of gear teeth reduce the beam span and increase relative stiffness of the documents which increases the force supplied to the documents in order to obtain a given deflection. This results in an overall increase in the frequency response of the system. The gear teeth of the sensor gears may take a variety of different shapes. For example, sensor gears having 29 teeth of the straight side variety have performed extremely well in detecting both limp and stiff bills. When two bills that were so limp that they would not move the detector far enough to cause the sensing circuit to function were run through a double feed, they were picked up as being too stiff. Thus, the limpness detection device is quite suitable for providing doubles detection as well as providing an indication of relative limpness or stiffness.

Operating speed of the limpness detector is preferably slightly greater than conventional counting devices used to count paper currency. The apparatus of the present invention can also be utilized to detect the presence of partially overlapping bills as well as double-fed bills. The electronics of FIG. 2 enable the counting of pulses as each bill passes. When the overlapping portion passes between the gear-like sensor members, such as 14 and 34 of FIG. 1a, the increased stiffness detection is indicated by pulses. If pulses of normal range stiffness and increased (i.e. overlapping) stiffness sum to the amount of pulses of a normal bill, then the first bill can be counted as a bill and the same overlapping pulses of the second bill plus the remaining normal stiffness pulses can be counted as a bill, thus permitting the counting of bills fed in overlapping fashion without stopping the high-speed flow of the bills.

Figure 7A:
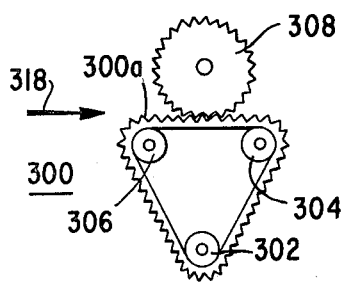
FIGS. 7a and 7b show end views of other alternative embodiments of the present invention.
Figure 7B:
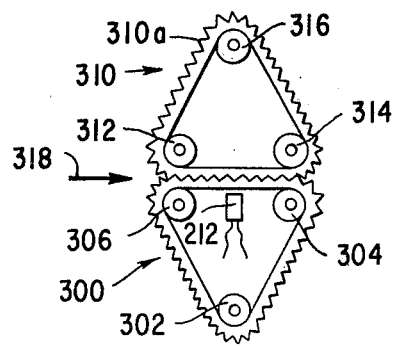

Although the preferred embodiments as described herein utilizes sensing gears of generally cylindrical shape, it is also possible to utilize timing belts of the type shown in FIGS. 7a and 7b for example, the lower sensor gear in the embodiment of FIG. 7a is replaced by a timing belt 300 having gear-like teeth 300a and entrained around the rollers 302, 304 and 306. The upper sensing gear is a gear 308 substantially resembling the upper sensor gear of the embodiments of FIGS. 1 through 6. In the embodiment of FIG. 7b, the lower sensor gear arrangement is substantially identical to that shown in FIG. 7a and the upper sensor gear 308 of FIG.

7a is replaced in FIG. 7b by a similar upper sensor gear arrangement comprised of an upper timing belt 310 having gear-like teeth 310a and entrained about rollers 312, 314 and 316. Documents are fed in the direction shown by arrow 318 in FIGS. 7a and 7b to move between the upper and lower sensor assemblies in order to undergo examination for limpness. In the embodiment of FIG. 7a, a proximity detector 212 may be positioned immediately adjacent the interior surface 300b of timing belt 300, which interior surface is provided with a conductive surface 300c cooperating with the proximity detector in a manner similar to the embodiment of FIG. 1b, for example.

Although the gear configuration is preferably a pointed gear, any other configuration can be employed such as a gear having a flat top surface and either straight or sloping sides, or a gear having a sinusoidal shaped periphery. The gears and/or timing belts may be formed of metal, plastic or rubber.

The preferred operating speed of the equipment is up to 200 linear inches per second. These speeds are capable of processing U.S. paper currency at the rate of 33 bills per second, or about 2000 per minute.

Figure 8:
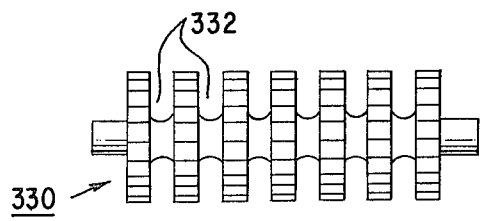
FIG. 8 shows a plan view of a modified roller.

In embodiments employing gear-like members of the type shown, for example, as the sensor gear 14 in FIG. 1a, in order to reduce the mass and weight of the gear, the arrangement of FIG. 8 may be employed wherein the sensor gear 330 is provided with a plurality of annular grooves 332, which grooves 332 are perpendicular to the axis of rotation of gear 330 and are provided to reduce the weight and hence mass of the gear-like member. The annular grooves 332 may be spaced a fraction of an inch apart from one another for example.

Figure 9:
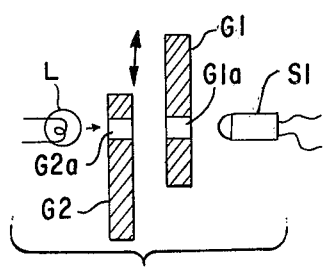
FIG. 9 shows a simplified end view of an optical sensor.

In the preferred embodiment of FIGS. 2 and 3, the proximity detector 81 employed therein is of the nature of a transformer excited by a five kilohertz signal generator. The detector may alternatively be any one of a variety of different devices including differential transformers, Hall effect sensors, micro-switches and optical gratings. Noting FIG. 9, for example, grating G1 may be coupled to move with the upper sensor gear 34, while grating G2 may be coupled to the upright to which the lower sensor gear 14 is rotatably mounted. Light source L1 is positioned to the left of grating G2. The amount of light passed by the openings G2a and G1a of gratings G2 and G1 is detected by light sensitive element S1. The amount of light passing to the light sensitive element S1 is determined by the relative alignment of the slits G1a and G2a in gratings G1 and G2.

FIGS. 10a-10c show still another embodiment 350 of the present invention in which gear-like roller 352 has its shaft 353 mounted within bearings 354, 356 provided in frame members 358, 360. Shaft 353 extends through frame member 360 and is journaled in bearing 362 provided in frame member 364. A pulley 366, secured to shaft 353, cooperates with timing belt 368 to rotate shaft 353 and roller 352.

L-shaped arm 370 is pivotally mounted upon shaft 372 which extends between frame members 360 and 364. The free end of short arm 370a pivotally supports shaft 374 which extends through clearance openings 364a and 360a provided in frame members 364 and 360. Swingable gear-like roller 376 is mounted at the free end of shaft 374.

A second arm 378 is secured to shaft 372 and cooperates with short arm portion 370a of L-shaped arm 370 to provide a swingable support for shaft 374 and roller 376 to assure that roller 376 is maintained in spaced parallel fashion relative to roller 352, regardless of the swinging movement of roller 376 about the axis of rotation of shaft 372. Helical spring 380 is wound about shaft 372 and has one end 380a secured to frame member 364 and the opposite end 380b secured to shaft 372 by set screw 382.

Gears 384 and 386, respectively mounted upon and secured to shafts 353 and 374, are in meshing engagement so as to rotate shaft 374 and swingable roller 376, upon rotation of shaft 353.

An angle bracket 388 has a portion 388a secured to frame member 364 by fasteners 390. Outwardly extending portion 388b respectively supports a sensor assembly 392, dash-pot assembly 394 and stop assemblies 396, 398.

Stop assembly 396 comprises a threaded rod 396a threadedly engaging nuts 396b, 396c, 396d and a slotted opening 370c in long arm portion 370b of L-shaped arm 370. Threaded rod 396a extends through a clearance opening in bracket portion 388b. Helical spring 396e is compressed between nut 396d and bracket portion 388b to normally urge L-shaped arm 370 clockwise about shaft 372, as shown by arrow 404 in FIG. 10c. Nuts 396b and 396c cooperate with spring 396e and nut 396d to limit the movement of arm 370b in the counterclockwise direction shown by arrow 402.

Threaded member 398a and nuts 398b, 398c of stop assembly 398 limits the movement of arm 370b in the direction of arrow 404. The left-hand end of threaded member 398a abuts the right-hand surface of arm 370b.

Dash-pot assembly 394 comprises a housing 394a having an outwardly extending arm 394b whose free end threadedly engages a tapped opening 370d in arm 370b. Housing 394a is mounted upon portion 388a of bracket 388. Dash-pot assembly 394 dampens the vibration of L-shaped arm 370 to reduce its sensitivity, rotatable member 394c being adjustable to alter the degree of attenuation of the swingable roller assembly.

A permanent magnet member 392a forming part of sensor assembly 392 is secured to arm 370b in recess 370e. A Hall-effect sensor device 392b is mounted to bracket portion 388b. The outer periphery of sensor 392b is threaded and is adjustably secured to arm portion 388b by nuts 392c, 392d.

The operation of the limpness detector is as follows. A motor (not shown) drives belt 368 rotating pulley 366, shaft 353 and gear-like roller 352. Gear 386 meshes with gear 384 and is rotated thereby to rotate shaft 374 and swingable gear-like roller 376.

The relative stiffness (or limpness) of sheets moving between rollers 352 and 376 controls the amount of displacement of roller 376 from roller 352. Spring biased limit assembly 396 limits the angle which L-shaped arm 370 can swing in the counterclockwise direction 402 to prevent gears 384 and 386 from disengaging during normal operation. However, in the event of a jam, arm 370b can be displaced to a point beyond its normal limit to prevent the limpness detector assembly from being damaged. The sensor 392 generates a signal which is a function of the separation distance between sensor 392b and permanent magnet 392a. The gears 384, 386 are aligned with their rollers 352, 376 so that when gears 384, 386 are in proper meshing engagement, rollers 352, 376 are likewise properly meshed.

The sensor assembly 392 is positioned a distance $D_1$ from the axis of shaft 372 while shaft 374 is positioned a distance $D_2$ from the axis of shaft 374, wherein $D_1$ is greater than D₂ to greatly increase the sensitivity of sensor assembly 392.

A latitude of modification, change, and substitution is intended in the foregoing disclosure and in some instances some features of the invention will be employed without a corresponding use of other features. Accordingly, it is appropriate that the appended claims be construed broadly and in a manner consistent with the spirit and scope of the invention herein. For example, the swingable sensor gear may be positioned below or at one side of the stationary sensor gear, wherein resilient means such as an O-ring 72 is employed to urge the sensor gears towards one another. The threshold circuits of FIG. 2 and the resiliency of O-ring 72 may be adjusted to test the limpness of a variety of different documents or sheets.

What is claimed is:

1. Apparatus for determining the limpness of moving sheets comprising:
first and second moving members, each of said members having an undulating peripheral surface and being displaceable relative to one another;
means yieldably urging said members towards one another whereby moving sheets passing therebetween are urged to assume an undulating contour due to said members; and
sensing means responsive to the spacing between said members due to the relative stiffness of a sheet tending to urge said members apart for generating a signal representing the limpness of the sheet moving between said members.

2. The apparatus of claim 1 comprising means for swingably mounting one of said members and said sensing means about a common pivot, said sensing means being positioned a greater distance from said pivot than said one of said members; and
a stationary member cooperating with said sensing means whereby the displacement of said sensing means from said stationary member determines the magnitude of said signal.

3. The apparatus of claim 2 wherein said swingable mounting means comprises arm means coupled to swing about said pivot and said one member being rotatably mounted on said arm means a predetermined distance from said pivot point and said sensing means being mounted on said arm means a second predetermined distance from said pivot point, said second predetermined distance being greater than said first predetermined distance.

4. The apparatus of claim 3 wherein said arm means comprises an L-shaped arm.

5. The apparatus of claim 4 wherein said L-shaped arm has two arm portions joined to form a knee region and the knee region of said L-shaped arm is joined to said pivot.

6. The apparatus of claim 5 wherein said sensing means is joined to one arm portion of said L-shaped arm and said member is rotatably mounted to the remaining arm portion of said L-shaped arm.

7. The apparatus of claim 2 wherein said sensing means comprises a hall-effect sensor.

8. The apparatus of claim 2 further comprising a dash-pot coupled to said means for swingably mounting said one of said members to reduce the sensitivity of said apparatus.

9. Apparatus for measuring limpness of moving sheets comprising:
a pair of moving surfaces arranged in spaced parallel fashion, said surfaces each having undulating peripheries which interleave one another;
means for yieldably urging said surfaces towards one another;
means directing said moving sheets into the nip formed by the interleaved peripheries of said moving surfaces whereby each sheet tends to exert a force urging said moving surfaces apart wherein the magnitude of said force is a function of the limpness of the sheet being examined; and
sensing means responsive to the relative spacing of said moving surfaces due to a sheet for generating a signal representing the limpness of the sheet being examined.

10. The apparatus of claim 9 wherein said moving surfaces have corrugated peripheries forming uniformly spaced peaks separated from one another by uniformly spaced recesses.

11. The apparatus of claim 10 further comprising means for moving said moving surfaces at a substantially constant rate so that the peaks of each moving surface at least partially enter into recesses of the other moving surface in the region of said nip in a continuous fashion, to urge a sheet passing through said nip to assume a corrugated shape.

12. The apparatus of claim 9 wherein the peripheries of said moving surfaces have a sawtooth type shape defined by uniformly spaced teeth each spaced from one another by uniformly spaced recesses such that the teeth of each moving surface at least partially enter into the recesses of the other moving surface in the region of said nip to urge a sheet passing therebetween to assume a corrugated shape.

13. The apparatus of claim 12 wherein said teeth have a triangular shape.

14. The apparatus of claim 12 wherein said recesses have a triangular shape.

15. The apparatus of claim 9 wherein said moving surfaces are rollers of a gear-shaped cross section; a first one of said rollers being arranged to rotate about a fixed axis;
means for rotating the remaining one of said rollers about a swingably mounted axis; and
said yieldable means urging said swingably mounted roller towards said first one of said rollers.

16. The apparatus of claim 15 comprising adjustable stop means for adjusting the minimum and maximum displacement distance between said rollers.

17. The apparatus of claim 15 further comprising adjustable stop means for adjusting the minimum displacement distance between said rollers.

18. The apparatus of claim 15 wherein said sensing means comprises signal generating means responsive to the position of said swingably mounted roller for generating said limpness signal.

19. The apparatus of claim 18 wherein said signal generating means comprises proximity detection means for detecting the position of said swingably mounted roller.

20. The apparatus of claim 9 further comprising:
first and second gears;
drive means for driving said first gear;
said second gear meshing with said first gear to be driven by said first gear;
each moving surface being a roller;
first coupling means coupling one of said rollers to said first gear; and second coupling means for coupling the remaining one of said rollers to said second gear, whereby rotation of said first gear is imparted to said second gear and said remaining one of said rollers.

21. The apparatus of claim 20 wherein said first and second gears are arranged at fixed axes.

22. The apparatus of claim 20 wherein said one of said rollers is arranged to rotate about a swingable axis; and; said first coupling means comprising a flexible drive coupling.

23. The apparatus of claim 9 wherein each moving surface comprises a roller and further comprising a ferromagnetic member associated with one of said rollers; and said sensing means comprising a proximity detector positioned adjacent to said ferromagnetic member for generating a signal representing the gap distance between said ferromagnetic member and said proximity detector.

24. The apparatus of claim 23, wherein said proximity detector is comprised of oscillator means;
output signal generating means;
transformer means comprising a first winding coupled to said oscillator means and a second winding coupled to said output signal generating means; and
said ferromagnetic member being positioned adjacent to said first and second windings whereby the movement of said ferromagnetic member relative to said first and second windings alters the magnetic coupling between said first and second windings.

25. The apparatus of claim 24 wherein said output signal generating means is comprised of means for rectifying the output signal developed by said second winding.

26. The apparatus of claim 9 further comprising comparison means for comparing said signal against a first reference level for generating an output when said signal is below said reference level.

27. The apparatus of claim 9 further comprising comparison means for comparing said signal against a first reference level for generating an output when said signal is above said reference level.

28. The apparatus of claim 26 further comprising second comparison means for comparing said signal against a second reference level above said first reference level for generating an output when said signal is above said second reference level.

29. The apparatus of claim 9 wherein each of said moving surfaces comprises a roller and wherein said rollers are comprised of a gear-like periphery having teeth comprised of straight-sided splines.

30. The apparatus of claim 9 wherein each of said pair of moving surfaces comprise first and second timing belts having gear-like teeth on their outer surfaces;
roller members for supporting and moving adjacent surfaces of said timing belts whereby sheets moving between said adjacent surfaces are urged into a corrugated configuration.

31. The apparatus of claim 30 wherein a surface of one of said belts is coated with a ferromagnetic material; and
said sensing means comprising proximity detector means positioned adjacent to said ferromagnetic coating for detecting the fluctuation of said belt due to the passage of sheets between said adjacent surfaces.

32. The apparatus of claim 9 wherein said sensing means comprises optical sensing means.

33. The apparatus of claim 32 wherein said optical sensing means comprises first and second gratings relatively movable responsive to the displacement experienced by said members; a light source for directing light toward said gratings; and
sensing means for detecting the amount of light passing through said gratings.

34. The apparatus of claim 9 wherein said pair of moving surfaces comprise a plurality of wires and means for maintaining said wires arranged at parallel equispaced intervals about an imaginary circle.

* * * * *

UNITED STATES PATENT AND TRADEMARK OFFICE
CERTIFICATE OF CORRECTION

PATENT NO. : 4,365,508

DATED : December 28, 1982

INVENTOR(S) : Peter J. Loftus

It is certified that error appears in the above-identified patent and that said Letters Patent is hereby corrected as shown below:

Column 7, line 34, "130e" should read --130c--.

Signed and Sealed this

Twenty-sixth Day of July 1983.

[SEAL]

Attest:

Attesting Officer

GERALD J. MOSSINGHOFF

Commissioner of Patents and Trademarks